US00PP29652P3

(12) United States Plant Patent
Hoogenraad

(10) Patent No.: US PP29,652 P3
(45) Date of Patent: Sep. 11, 2018

(54) ***THUJA* PLANT NAMED 'HOOGI023'**

(50) Latin Name: *Thuja occidentalis*
Varietal Denomination: Hoogi023

(71) Applicant: Mark Sebastiaan Hoogenraad, Ederveen (NL)

(72) Inventor: Mark Sebastiaan Hoogenraad, Ederveen (NL)

( * ) Notice: Subject to any disclaimer, the term of this patent is extended or adjusted under 35 U.S.C. 154(b) by 0 days.

(21) Appl. No.: 15/530,899

(22) Filed: Mar. 20, 2017

(65) Prior Publication Data

US 2017/0295683 P1 Oct. 12, 2017

(30) Foreign Application Priority Data

Apr. 11, 2016 (EM) ..... 2016/0921

(51) Int. Cl.
*A01H 7/00* (2006.01)
*A01H 5/02* (2018.01)

(52) U.S. Cl.
USPC ..... Plt./213
CPC ..... *A01H 5/025* (2013.01)

(58) Field of Classification Search
USPC ..... Plt./213
See application file for complete search history.

*Primary Examiner* — Anne Marie Grunberg
(74) *Attorney, Agent, or Firm* — Penny J Aguirre

(57) ABSTRACT

A new cultivar of *Thuja occidentalis* plant named, 'Hoogi023', that is characterized by its compact and columnar plant habit, and its new foliage that is golden yellow in summer turning more yellow-orange in fall and winter.

2 Drawing Sheets

Botanical classification: *Thuja occidentalis.*
Varietal denomination: 'Hoogi023'.

BACKGROUND OF THE INVENTION

The present invention relates to a new and distinct cultivar of *Thuja occidentalis* and will be referred to hereafter by its cultivar name, 'Hoogi023'. 'Hoogi023' represents a new cultivar of northern white cedar, an evergreen tree grown for landscape use and particularly useful for hedging.

The new *Thuja* originated as a naturally occurring branch mutation of *Thuja occidentalis* 'Smaragd' (not patented) that was growing in a container at the Inventor's nursery in Ederveen, The Netherlands.

Asexual propagation of the new cultivar was first accomplished by softwood stem cuttings by the Inventor in 2012 in Ederveen, The Netherlands. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Hoogi023' as a unique and distinct cultivar of *Thuja.*

1. 'Hoogi023' exhibits a compact and columnar plant habit.
2. 'Hoogi023' exhibits new foliage that is golden yellow in summer turning more yellow-orange in fall and winter.

'Smaragd', the female parent of 'Hoogi023', differs from 'Hoogi023' in having foliage that are green in color. 'Hoogi023' can also be compared to the cultivars 'Janed Gold' (U.S. Plant Pat. No. 21,967) and 'Golden Brabant' (U.S. Plant Pat. No. 24,746). 'Janed Gold' is similar to 'Hoogi023' in having a columnar plant habit and yellow foliage. 'Janed Gold' differs from 'Hoogi023' in having an even more narrow plant habit and in having duller yellow foliage. 'Golden Brabant' is similar to 'Hoogi023' in having yellowish foliage. 'Golden Brabant' differs from 'Hoogi023' in having foliage that is yellow-green on mature and young foliage, foliage that is less yellow in color, and in having a broader plant habit.

BRIEF DESCRIPTION OF THE DRAWINGS

The accompanying colored photographs illustrate the overall appearance and distinct characteristics of the new *Thuja.* The photographs were taken of a plant 18-months in age as grown outdoors in a 19-cm container in Ederveen, The Netherlands.

The photograph in FIG. 1 provides a side view of the plant habit of 'Hoogi023'.

Figure 1:
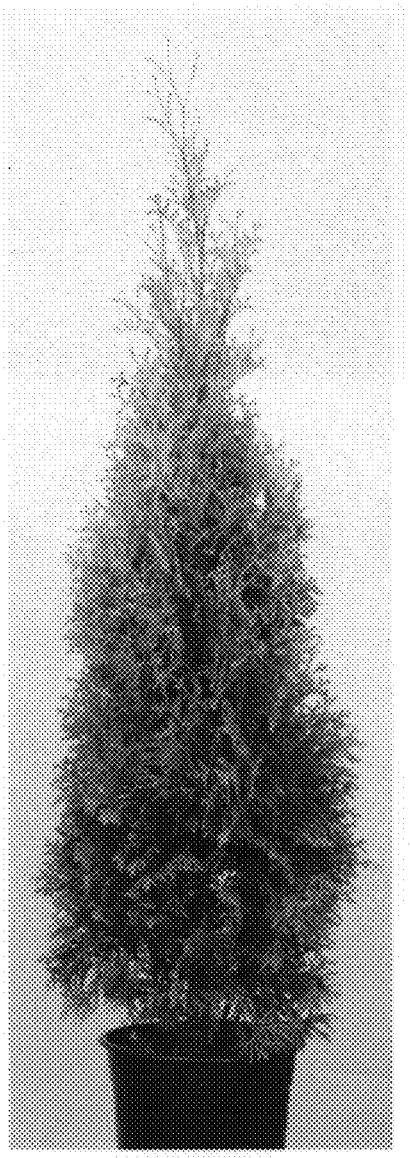
Figure 2:
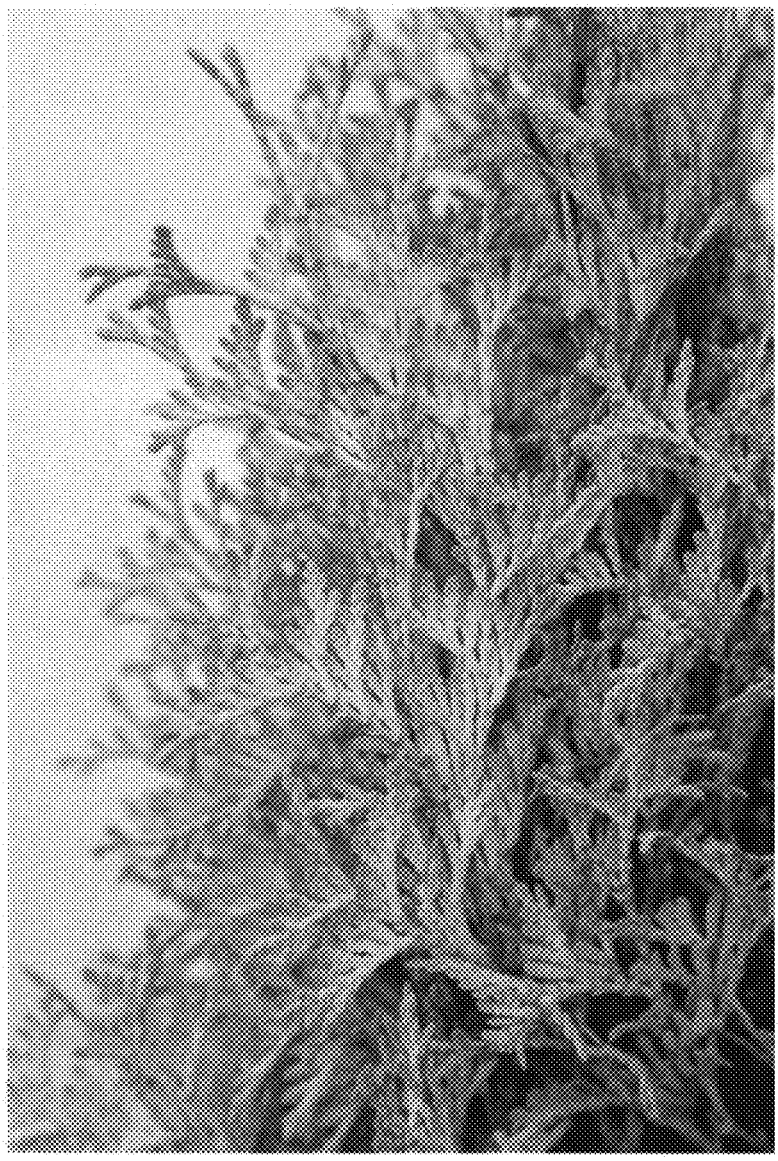

The photograph in FIG. 2 provides a close-up view of the young foliage of 'Hoogi023' in summer.

The colors in the photographs are as close as possible with the digital photography and printing techniques utilized and the color codes in the detailed botanical description accurately describe the colors of the new *Thuja.*

BOTANICAL DESCRIPTION OF THE PLANT

The following is a detailed description of 18 month-old plants of the new cultivar as grown outdoors in February in 19-cm circular containers in Ederveen, The Netherlands. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Plant type.*—Evergreen tree.

*Plant and growth habit.*—Narrow conical to conical, woody plant with main branches and lateral branches.

*Height and spread.*—An average of 103 cm in height and 36 cm in spread as grown in a 19-cm container.

*Cold hardiness.*—U.S.D.A. Zones 3 to 11.

*Diseases and pest resistance.*—No susceptibility or resistance to diseases and pests has been observed.

*Root description.*—Fibrous and fine.

*Growth rate.*—Moderately vigorous.

*Propagation.*—Softwood stem cuttings.

*Root development.*—An average of 4 weeks to produce a rooted cutting and about 12 months weeks to produce a fully rooted plant in a 12.5-cm container.

Branch description:

*Branch color.*—New wood; 152A to 152C, mature; between 166C and N199D, internodes; 199B, older stems and bark; between 176A and 200C to 200D.

*Branch size.*—An average of 36.9 cm in length and 4 mm in diameter, main trunk branch (trunk); an average of 4 cm in width at soil line.

*Stem aspect.*—Lateral branches are held in an average angle of 40° to soil level (=0°).

*Number of branches.*—Primary branches; 1, secondary branches; 38.

*Branch surface.*—Slightly glossy.

*Branch shape.*—Rounded.

*Branch internode length.*—An average 2.3 cm.

*Branch habit.*—Freely branching, lateral branches emerge from the base and from the main stems.

*Branch strength.*—Strong.

Foliage description:

*Leaf shape.*—Oblong and folded.

*Leaf division.*—Simple.

*Leaf base.*—Decurrent.

*Leaf angle.*—Held in an average angle of 20° to lateral branch (=0°).

*Leaf apex.*—Apiculate.

*Leaf venation.*—No veins visible.

*Leaf margin.*—Entire.

*Leaf attachment.*—Petiolate.

*Leaf arrangement.*—Opposite.

*Leaf surface.*—Upper and lower surface smooth, matte and glabrous.

*Leaf size.*—An average of 3 cm in length and 2 cm in width.

*Leaf number.*—Over 15,000 scale-like leaves per lateral branch.

*Leaf color.*—Young foliage upper and lower surface; 7B to 7C, mature foliage upper and lower surface; between 144B and 151A, fall color; seasons near growth turns to 163B.

*Leaf fragrance.*—When crushed, the leaves smell pleasant, typical for *Thuja occidentalis* varieties.

*Stipules.*—None present.

Cone description: Neither male nor female cones have been observed to date.

It is claimed:

1. A new and distinct cultivar of *Thuja* plant named 'Hoogi023' substantially as herein illustrated and described.

* * * * *